US012646597B2

(12) United States Patent
Alwan

(10) Patent No.: US 12,646,597 B2
(45) Date of Patent: Jun. 2, 2026

(54) PATIENT-DEVICE ASSOCIATION SYSTEM

(71) Applicant: CareFusion 303, Inc., San Diego, CA (US)

(72) Inventor: James J. Alwan, Ramona, CA (US)

(73) Assignee: CAREFUSION 303, INC., San Diego, CA (US)

( * ) Notice: Subject to any disclaimer, the term of this patent is extended or adjusted under 35 U.S.C. 154(b) by 0 days.

(21) Appl. No.: 18/236,350

(22) Filed: Aug. 21, 2023

(65) Prior Publication Data

US 2023/0395216 A1 Dec. 7, 2023

Related U.S. Application Data

(63) Continuation of application No. 16/867,495, filed on May 5, 2020, now Pat. No. 11,735,296, which is a continuation of application No. 13/540,481, filed on Jul. 2, 2012, now Pat. No. 10,650,917.

(51) Int. Cl.
*G16H 10/60* (2018.01)
*G06Q 50/00* (2012.01)

(52) U.S. Cl.
CPC ............. *G16H 10/60* (2018.01); *G06Q 50/00* (2013.01)

(58) Field of Classification Search
CPC ..... G06F 19/3418; G16H 40/67; G16H 20/17
USPC ....................................................... 705/2, 3
See application file for complete search history.

(56) References Cited

U.S. PATENT DOCUMENTS

| | | | |
|---|---|---|---|
| 7,236,936 B2 | 6/2007 | White | |
| 7,895,053 B2 | 2/2011 | Holland | |

| | | | |
|---|---|---|---|
| 8,234,128 B2 | 7/2012 | Martucci | |
| 8,862,999 B2 | 10/2014 | Gupta | |
| 9,123,077 B2 | 9/2015 | Silkaitis | |
| 2009/0088607 A1 | 4/2009 | Muraca | |
| 2009/0119124 A1 | 5/2009 | Kambaloor | |

(Continued)

FOREIGN PATENT DOCUMENTS

| | | | | |
|---|---|---|---|---|
| AU | 2005311774 A1 * | 6/2006 | ............. | G16H 40/20 |
| AU | 2011201894 B2 * | 6/2012 | ......... | G06F 19/3418 |

(Continued)

OTHER PUBLICATIONS

Leicester E. Gill, "OX-Link: The Oxford Medical Record Linkage System", Internet Citation, XP002363419, retrieved from http://www.fcsm.gov/working-papers/RLT97_chap2.html, Mar. 21, 1997, pp. 15-33.

(Continued)

*Primary Examiner* — Dilek B Cobanoglu
(74) *Attorney, Agent, or Firm* — MASCHOFF BRENNAN

(57) ABSTRACT

A system for associating a patient with a device may include a memory and a processor. The memory may be configured to store a plurality of orders and a set of parameters, wherein each of the plurality of orders comprises order attributes and each of the plurality of orders identifies one of a plurality of patients. The processor may be configured to receive the plurality of orders from an order entry system, receive the set of parameters from a device, correlate the set of parameters with an order of the plurality of orders based on the order attributes of the plurality of orders, associate the device with the patient identified by the order that correlates with the set of parameters, and provide, to the device, an indication of the patient associated with the device.

20 Claims, 7 Drawing Sheets

(56) References Cited

U.S. PATENT DOCUMENTS

| | | |
|---|---|---|
| 2009/0156991 A1 | 6/2009 | Roberts |
| 2011/0152830 A1* | 6/2011 | Ruchti ................... G16H 20/17 |
| | | 604/93.01 |
| 2012/0209625 A1 | 8/2012 | Armstrong |
| 2015/0161354 A1 | 6/2015 | Blomquist |
| 2016/0074573 A1* | 3/2016 | Kohlbrecher ......... G16H 40/67 |
| | | 604/151 |

FOREIGN PATENT DOCUMENTS

| | | | | |
|---|---|---|---|---|
| BR | PI0507175 A | * | 6/2007 | ......... A61M 5/1723 |
| WO | WO-2010/067230 A1 | | 6/2010 | |

OTHER PUBLICATIONS

Howe, et al., "A Generalized Iterative Record Linkage Computer System for Use in Medical Follow-up Studies," Computers and Biomedical Research, Academic Press, London, GB, vol. 14, No. 4, Aug. 1, 1981, pp. 327-340.
Google patents search, Oct. 21, 2019.
Google patents search, Dec. 11, 2017.
Google patents search, Feb. 9, 2017.
Google patents search, Aug. 22, 2016.
Google patents search, Mar. 18, 2022.
ip.com search, Mar. 18, 2022.

* cited by examiner

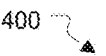

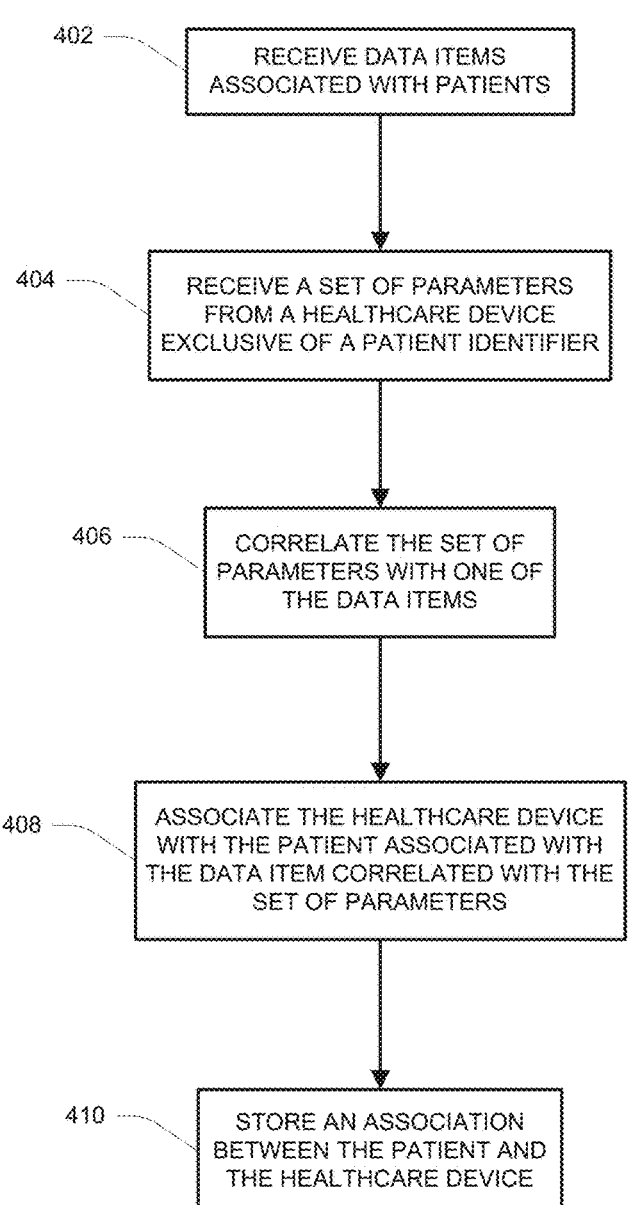

400

402 — RECEIVE DATA ITEMS ASSOCIATED WITH PATIENTS

404 — RECEIVE A SET OF PARAMETERS FROM A HEALTHCARE DEVICE EXCLUSIVE OF A PATIENT IDENTIFIER

406 — CORRELATE THE SET OF PARAMETERS WITH ONE OF THE DATA ITEMS

408 — ASSOCIATE THE HEALTHCARE DEVICE WITH THE PATIENT ASSOCIATED WITH THE DATA ITEM CORRELATED WITH THE SET OF PARAMETERS

410 — STORE AN ASSOCIATION BETWEEN THE PATIENT AND THE HEALTHCARE DEVICE

FIG. 4

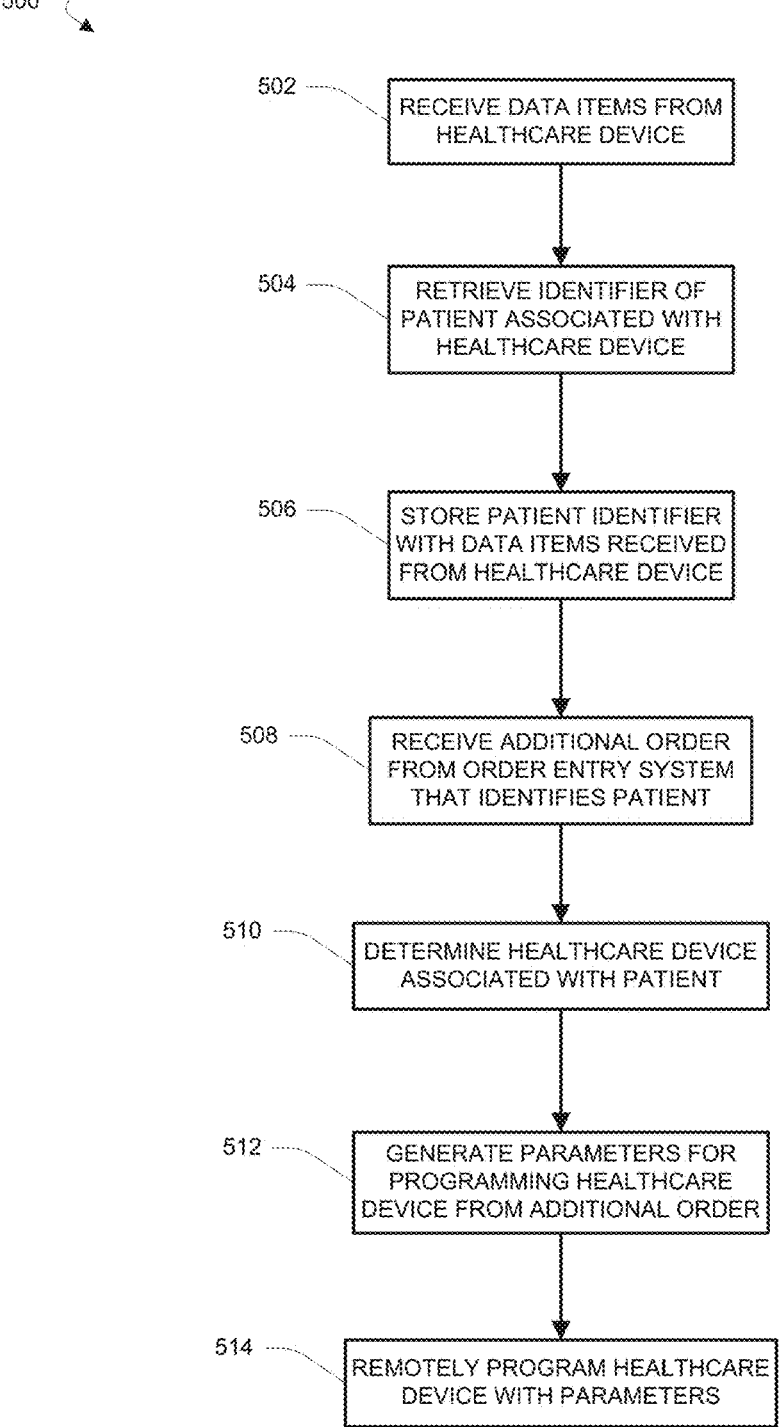

500

502 — RECEIVE DATA ITEMS FROM HEALTHCARE DEVICE

504 — RETRIEVE IDENTIFIER OF PATIENT ASSOCIATED WITH HEALTHCARE DEVICE

506 — STORE PATIENT IDENTIFIER WITH DATA ITEMS RECEIVED FROM HEALTHCARE DEVICE

508 — RECEIVE ADDITIONAL ORDER FROM ORDER ENTRY SYSTEM THAT IDENTIFIES PATIENT

510 — DETERMINE HEALTHCARE DEVICE ASSOCIATED WITH PATIENT

512 — GENERATE PARAMETERS FOR PROGRAMMING HEALTHCARE DEVICE FROM ADDITIONAL ORDER

514 — REMOTELY PROGRAM HEALTHCARE DEVICE WITH PARAMETERS

FIG. 5

600
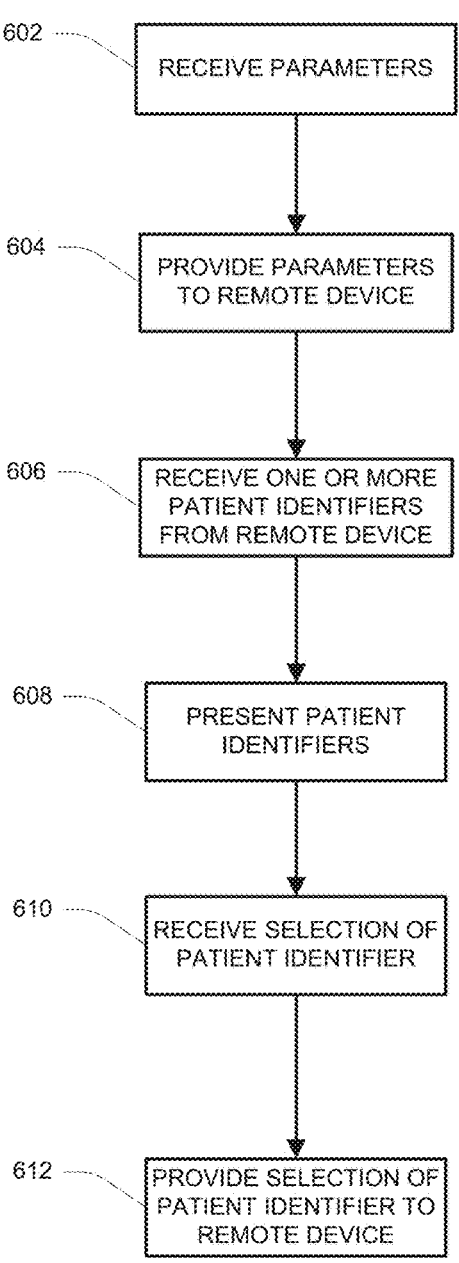
602 — RECEIVE PARAMETERS
604 — PROVIDE PARAMETERS TO REMOTE DEVICE
606 — RECEIVE ONE OR MORE PATIENT IDENTIFIERS FROM REMOTE DEVICE
608 — PRESENT PATIENT IDENTIFIERS
610 — RECEIVE SELECTION OF PATIENT IDENTIFIER
612 — PROVIDE SELECTION OF PATIENT IDENTIFIER TO REMOTE DEVICE
FIG. 6

PATIENT-DEVICE ASSOCIATION SYSTEM

CROSS-REFERENCE TO RELATED APPLICATIONS

This application is a continuation of application Ser. No. 16/867,495, filed on May 5, 2020, issued as U.S. Pat. No. 11,735,296 on Aug. 22, 2023, which is a continuation application of application Ser. No. 13/540,481, filed on Jul. 2, 2012, now U.S. Pat. No. 10,650,917, the entirety of each of which is incorporated herein by reference.

TECHNICAL FIELD

The present disclosure is related to associating patients with devices, and more particularly, to systems and methods for associating patients with devices by correlating patient de-identified data received from the devices with patient identified data received from independent data sources.

BACKGROUND

Hospitals and other caregiving institutions typically employ a number of different electronic device and data systems to carry out many of the functions of the hospital, such as Admit-Discharge-Transfer (ADT), physician order entry (POE), electronic Medicine Administration Record (eMAR), medication dispensing devices, patient monitoring devices, and others. For example, a POE system may generate orders for providing medications to patients, medication dispensing devices may be programmed to provide the medications to the patients, and patient monitoring devices may monitor the patients, such as while they receive the medications through the medication dispensing devices.

Although many of these devices may be capable of collecting a wealth of information corresponding to the healthcare being provided to the patients, the devices may not be aware of the identity of the patient for which the healthcare is being provided. Thus, data collected by these devices may be de-identified data, e.g. the data may not identify the patient to which the data corresponds. Accordingly, a hospital may be unable to identify the patients corresponding to the collected data, and therefore the hospitals may be unable to utilize the collected data, such as to assist with providing healthcare to the patients.

SUMMARY

The disclosed subject matter relates to a method for associating a patient with a device. The method may include receiving a plurality of orders, each comprising order attributes, from an order entry system, wherein each of the plurality of orders identifies one of a plurality of patients. The method may further include receiving a set of parameters from a device for providing healthcare. The method may further include correlating the set of parameters with an order of the plurality of orders based on the order attributes of the plurality of orders. The method may further include associating the device with the patient identified by the order that is correlated with the set of parameters, and providing, to the device, an indication of the patient associated with the device.

The disclosed subject matter also relates to a method for confirming a patient-device association. The method may include receiving a set of parameters that relate to providing healthcare to a patient. The method may further include providing the set of parameters to a remote device and receiving, from the remote device, one or more patient identifiers. The method may further include presenting the one or more patient identifiers and receiving a selection of one of the one or more patient identifiers that identifies the patient. The method may further include providing the selection of the one of the one or more patient identifiers to the remote device.

The disclosed subject matter also relates to a method for associating patients with devices. The method may include receiving a plurality of orders that each comprises a plurality of order attributes from an order entry system, wherein each of the plurality of orders identifies one of a plurality of patients. The method may further include receiving sets of parameters from a plurality of devices, and correlating each set of parameters with the plurality of order attributes of one or more of the plurality of orders. The method may further include disambiguating each set of parameters that is correlated with more than one of the plurality of orders, wherein the disambiguating is based on an attribute associated with the device from which each set of parameters that is correlated with more than one of the plurality of orders was received. The method may further include generating a data structure comprising associations between each of the plurality of devices from which each set of parameters was received and the patient of the plurality of patients identified by the order of the plurality of orders correlated with each set of parameters, and storing the data structure in a memory.

The disclosed subject matter also relates to a system for associating a patient with a device. The system may include means for receiving a plurality of orders, each comprising order attributes, from an order entry system, wherein each of the plurality of orders identifies one of a plurality of patients. The system may further include means for receiving a set of parameters from a device for providing healthcare, and means for correlating the set of parameters with an order of the plurality of orders based on the order attributes of the plurality of orders. The system may further include means for associating the device with the patient identified by the order that is correlated with the set of parameters, and means for providing, to the device, an indication of the patient associated with the device.

The disclosed subject matter also relates to a system for associating a patient with a device. The system may include a memory and a processor. The memory may be configured to store a plurality of orders and a set of parameters, wherein each of the plurality of orders comprises order attributes and each of the plurality of orders identifies one of a plurality of patients. The processor may be configured to receive the plurality of orders from an order entry system, receive the set of parameters from a device, correlate the set of parameters with an order of the plurality of orders based on the order attributes of the plurality of orders, associate the device with the patient identified by the order that is correlated with the set of parameters, and provide, to the device, an indication of the patient associated with the device.

The disclosed subject matter also relates to a machine-readable medium comprising instructions stored therein, which when executed by a machine, allow the machine to perform a method for associating a patient with a device. The method may include receiving a plurality of orders, each comprising order attributes, from an order entry system, wherein each of the plurality of orders identifies one of a plurality of patients. The method may further include receiving a set of parameters from a device for providing healthcare. The method may further include correlating the set of parameters with an order of the plurality of orders based on the order attributes of the plurality of orders. The method may further include associating the device with the patient identified by the order that is correlated with the set of parameters, and providing, to the device, an indication of the patient associated with the device.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIG. 4 illustrates a flow diagram of an alternative example server process for associating a patient with a device in a patient-device association system.

FIG. 5 illustrates a flow diagram of an example server process for handling data corresponding to a patient associated with a healthcare device in a patient-device association system.

FIG. 6 illustrates a flow diagram of an example device process for confirming a patient-device association in a patient-device association system.

DETAILED DESCRIPTION

Figure 1:
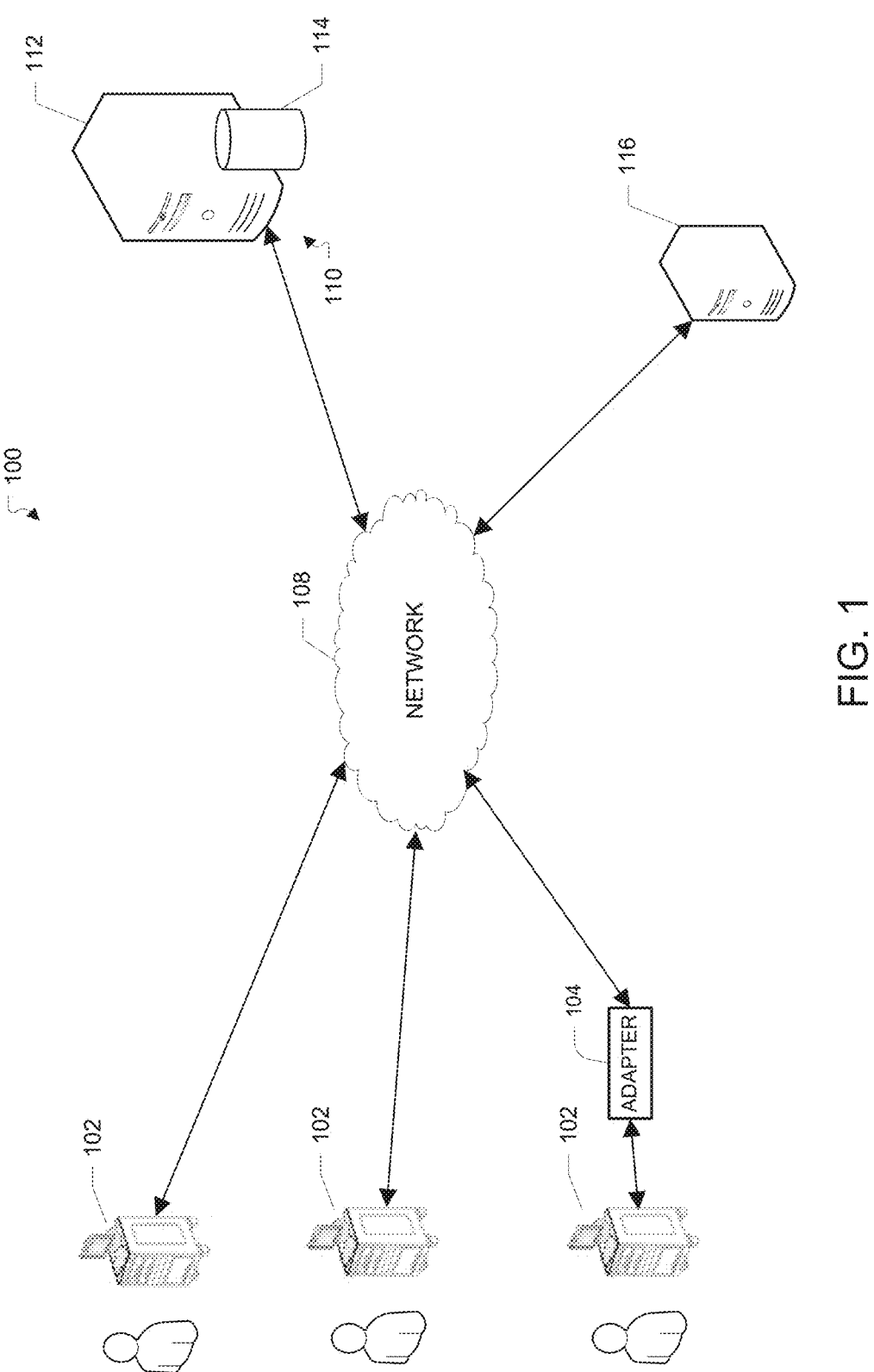
FIG. 1 illustrates an example network environment in a hospital or caregiving institution that may implement a patient-device association system.

Hospitals and caregiving institutions may employ a wide range of healthcare devices and systems for providing healthcare to patients. These healthcare devices may continuously generate data corresponding to the patients for which they are providing healthcare. For example, a blood pressure monitoring device may continuously generate data corresponding to a patient's blood pressure, while a medication dispensing device may continuously generate data corresponding to the amount of medication being dispensed to the patient. Although healthcare devices may have traditionally been standalone devices, advancements in network infrastructures in hospitals and caregiving institutions have resulted in the interconnection of healthcare devices such that the data generated by the healthcare devices can be aggregated in a backend server, such as a remote database.

However, since healthcare devices may have traditionally been standalone devices, both the healthcare devices and the backend server may be lacking a mechanism for identifying the patients corresponding to the data generated by the healthcare devices. Thus, both the healthcare devices and the backend server may be unable to associate data generated by a healthcare device with a corresponding patient. Some healthcare devices may be interoperable with an input device, such as a keypad or a bar code scanner, which may be used to identify the patient receiving healthcare from the healthcare device. However, there may be additional costs associated with providing an input device for each healthcare device. In addition, it may be time consuming and/or unwieldy for a healthcare professional to input a patient's identity for each healthcare device. Further in this regard, the accuracy of identifying a patient through an input device may be dependent on the healthcare professional operating the input device. For example, it may be ineffective to identify a patient through an input device if healthcare professionals neglect to input the identity of patients, or healthcare professionals incorrectly input the identity of patients.

In a patient-device association system, healthcare devices may be in communication with a backend server, such as through a hospital's computer network. When a healthcare professional programs parameters into a healthcare device to provide healthcare to a patient, the parameters may be communicated over the network to the backend server, without identifying the patient receiving the healthcare, which may be unknown to the healthcare device. Since the parameters do not identify a patient, the parameters may be referred to as patient de-identified data. The parameters may be information that is programmed into the healthcare devices by healthcare providers as a matter of course, such as parameters for dispensing mediation to a patient, or parameters for monitoring a patient.

The backend server may receive the parameters from the healthcare device and may correlate the patient de-identified parameters with information that identifies a patient, e.g. patient identified-information, such as an order received through a POE system, or a profile of a patient. If the server is able to correlate the parameters with stored information that identifies a single patient, the server may store an association between the healthcare device and the patient. However, if the server correlates the parameters to stored information that identifies multiple patients, the server may utilize extrinsic or intrinsic attributes of the healthcare device, and/or any additional information determinable from the stored information, to correlate the parameters with stored information that identifies a single patient. The server may then associate the healthcare device with the single patient and the server associate any data subsequently generated by the healthcare device with the single patient.

Accordingly, a hospital or caregiving institution implementing the patient-device data association system described herein may be able to determine a patient-device association by correlating patient de-identified data received from a healthcare device with patient identified data received from one or more independent data sources, without the need for additional hardware, such as input devices, and without the need for additional input, e.g. non-traditional input, from healthcare professionals.

FIG. 1 illustrates an example network environment in a hospital or caregiving institution that may implement a patient-device association system. Network environment 100 may include a number of healthcare devices 102 communicably connected to server 110, such as by network 108. Healthcare devices 102 may include medication dispensing devices, patient monitoring devices, asset monitoring devices, or generally any device that provides healthcare to patients, or any device that is associated with providing healthcare to patients. The healthcare devices 102 may be programmable, such as by a healthcare professional, e.g. a nurse or a doctor, a caregiver, or generally any other person. For example, a medication dispensing device may be programmed with parameters that relate to the dispensing of the medication, such as the amount of the medication to be dispensed, the rate at which the medication is to be dispensed, or the time period when the medication is to be dispensed.

Network 108 may be a public communication network (such as the Internet, cellular data network, dialup modems over a telephone network) or a private communications network (such as private local area network ("LAN"), leased lines). Network 108 may also include, but is not limited to, any one or more of the following network topologies, including a bus network, a star network, a ring network, a mesh network, a star-bus network, a tree or hierarchical network, and the like.

In some examples, healthcare devices 102 can be computing devices such as laptop or desktop computers, smartphones, personal digital assistants ("PDAs"), medication dispensing systems, tablet computers, health monitoring systems, or other devices with one or more processors coupled thereto or embedded therein, or other appropriate computing devices that can be used in a hospital or caregiving institution. Alternatively, or in addition, healthcare devices 102 may be any devices capable of any form of direct, or indirect, communication with the server 110. In the example of FIG. 1, healthcare devices 102 are depicted as medication dispensing devices.

Alternatively, or in addition, one or more of the healthcare devices 102 may be coupled to an adapter 104 for communicating with the server 110. For example, a legacy healthcare device that is not capable of communication with the server 110 and/or does not include one or more processors may be communicably connected to an adapter 104. The adapter 104 may include a memory, one or more processors, an interface for communicating with the legacy healthcare device, and an interface for communicating with the server 110, such as over the network 108. The adapter 104 may receive data collected by the legacy healthcare device and may communicate the data over the network 108 to the server 110. The adapter 104 may also receive instructions, such as parameters, from the server 110, such as over the network 108, and may program the legacy healthcare device in accordance with the received instructions. The adapter 104 may thereby allow a legacy healthcare device to communicate data to the server 110 and to be remotely programmed with parameters provided by the server 110.

In one example, server 110 includes processing device 112 and data store 114. Processing device 112 executes computer instructions stored in data store 114. Data store 114 may store the computer instructions on non-transitory computer-readable medium. Data store 114 may also store data received from the healthcare devices 102, along with associations between the healthcare devices 102 and patients.

Sever 116 may be communicably coupled with server 110, such as via network 108. Although only one instance of server 116 is illustrated in FIG. 1, the network environment 100 may include multiple servers 116 that are each associated with a function of the hospital or caregiving institution. For example, network environment 100 may include one or more servers 116 associated with a physician order entry (POE) system, one or more servers 116 associated with an Admit-Discharge-Transfer (ADT) system, and/or one or more servers 116 associated with an electronic Medicine Administration Record (eMAR) system. Alternatively, or in addition, one or more of the hospital systems may be consolidated on a single server 116, and/or one or more of the systems may be consolidated within server 110.

Server 116 may generally provide data items that identify patients, e.g. patient-identified data items, to the server 110, such as the physician orders of the POE system, or admit, discharge, or transfer orders of the ADT system. The server 116 may provide the data items to the server 110 via network 108. The server 110 may store the data items that identify patients in the data store 114.

In operation, the server 110 may receive data items from the server 116 that identify a particular patient, such as orders for patients entered into a POE system. The server 110 may also receive, from the healthcare devices 102, parameters that are programmed into the healthcare devices 102, such as parameters related to dispensing medication in the example of a medication dispensing device. The server 110 may receive the parameters from the healthcare devices 102 exclusive of any patient identifying information, e.g. the server 110 may receive the parameters as patient de-identified data items.

The server 110 may correlate parameters received from a healthcare device 102 with stored data items that identify patients, such as orders received from a POE system. If the server 110 is able to correlate the parameters with stored data items corresponding to a single patient, the server 110 may store an association between the healthcare device 102 and the single patient. If the parameters correlate with data items corresponding to multiple patients, the server 110 may utilize extrinsic and/or intrinsic attributes of the healthcare device 102 and/or additional information determinable from the data items, to correlate the parameters with stored information corresponding to a single patient. The process of associating a patient with a healthcare device 102 is discussed further in FIGS. 2-4 below. After associating a patient with a healthcare device 102, the server 110 may subsequently associate any data generated by the healthcare device 102 with the patient, such as by storing an association between the data and the patient in the data store 114. The process of handling data corresponding to a patient associated with a healthcare device 102 is discussed further in FIG. 5 below.

In one example, the server 110 may provide an indication of the associated patient to the healthcare device 102. The healthcare device 102 may present the indication of the associated patient to a healthcare professional, such as on a display. The healthcare professional may view the indication of the associated patient on the display and may confirm whether the indicated patient corresponds to the patient receiving healthcare from the healthcare device 102. The confirmation may be communicated to the server 110. The process of confirming a patient-device association is discussed further in FIG. 6 below.

Figure 2:
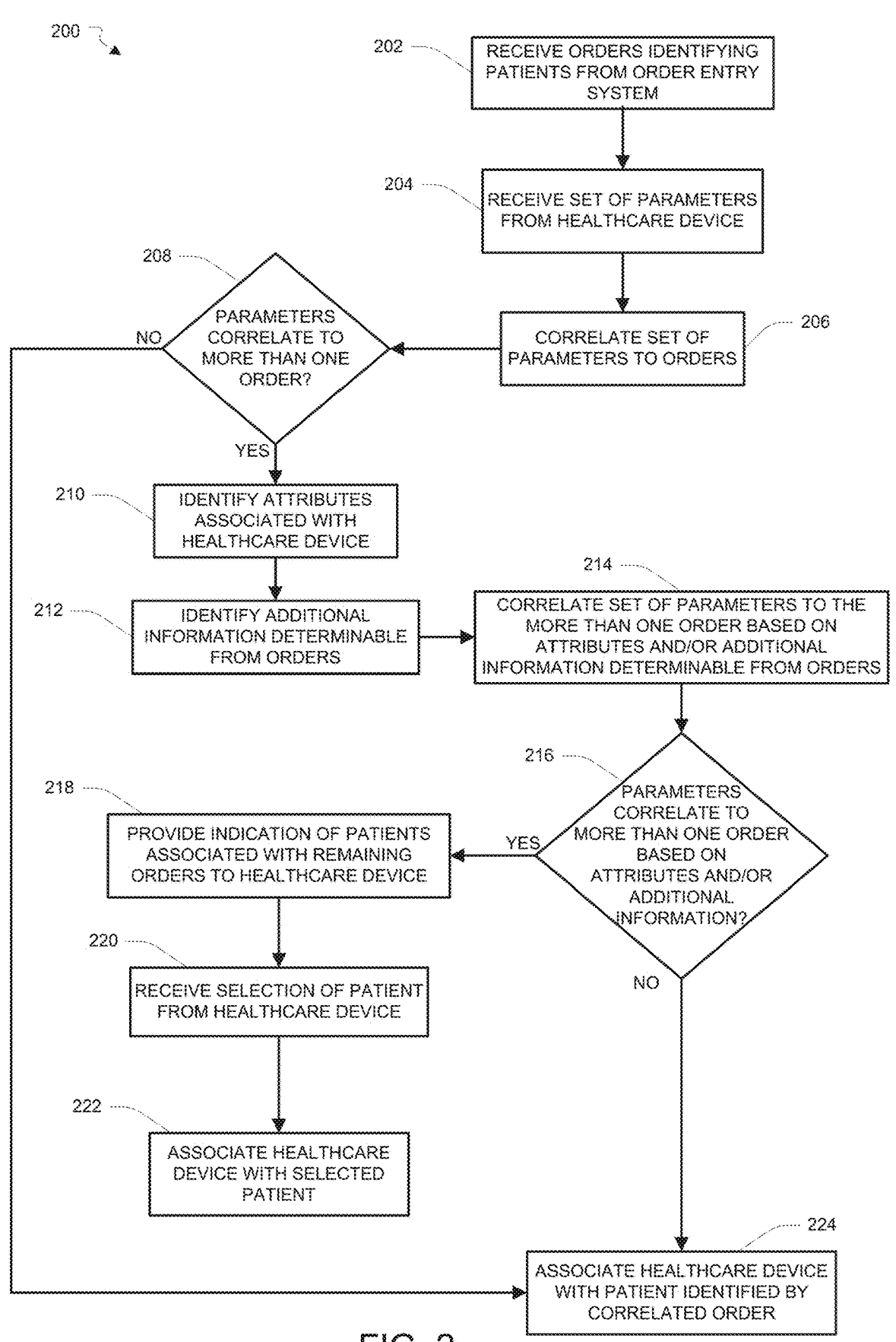
FIG. 2 illustrates a flow diagram of an example server process for associating a patient with a device in a patient-device association system.

FIG. 2 illustrates a flow diagram of an example server process 200 for associating a patient with a device in a patient-device association system. At step 202, server 110 may receive orders that identify patients from an order entry system, such as server 116. In addition to identifying patients, the orders may each include one or more order attributes, such as a medication ordered, an amount of the medication ordered, a time period when the medication is to be dispensed, a rate at which the medication is to be dispensed, or generally any attributes that may be included in an order.

At step 204, the server 110 may receive a set of parameters from a healthcare device 102. For example, a healthcare professional or other user may program a healthcare device 102, such as a patient monitoring device or a medication dispensing device, with a set of parameters.

In the instance of a medication dispensing device, a healthcare professional may program the healthcare device 102 with parameters related to one or more of the type of medication that will be dispensed to the patient, the amount of the medication that will be dispensed to the patient, the time period when the medication will be dispensed to the patient, the rate at which the medication will be dispensed to the patient, characteristics of the patient, e.g. height, weight, etc, or generally any information that relates to dispensing medication to the patient. In one example, the healthcare professional may program the healthcare device 102 with parameters derived from attributes of an order that was generated by the POE system, such as server 116. Accordingly, there may be a correlation between the set of parameters received by the server 110 from the healthcare device 102, and the order attributes of one of the orders received by the server 110 from the POE system.

In the instance of a patient monitoring device, a healthcare professional may program the healthcare device 102 with parameters related to characteristics of the patient, such as the height of the patient, the weight of the patient, the age of the patient, the blood type of the patient, or generally any characteristic of the patient that may be used, or requested, by a patient monitoring device.

At step 206, the server 110 correlates the set of parameters received from the healthcare device 102 to orders received from the POE system. Since the parameters programmed into the healthcare device 102 may have been derived from attributes of an order generated by the POE system, the server 110 may be able to correlate the parameters to attributes of one of the orders received from the POE system. For example, the server 110 may search for an order that includes order attributes that correlate to the received parameters, e.g. an order for which one or more of the type of medication, the amount of medication to be dispensed, the rate of dispensing the medication, the time period for dispensing the medication, and/or any other attributes corresponding to the dispensing of the medication correlate to the values of the set of parameters.

At step 208, the server 110 determines whether the set of parameters correlates to more than one order. The server 110 may determine that the set of parameters correlates to only one order when only one order includes attributes that correlate directly to the set of parameters. If, at step 208, the server 110 determines that the set of parameters correlates to only one order, the server 110 may proceed to step 224.

At step 224, the server 110 may associate the health care device 102 from which the set of parameters was received with the patient that is identified by the correlated order. Alternatively, or in addition, the server 110 may provide an indication of the patient to the healthcare device 102 and the healthcare device 102 may present the indication of the patient to the healthcare professional that programmed the healthcare device 102. The healthcare professional may confirm that the indicated patient corresponds to the patient receiving healthcare from the healthcare device 102, such as by pressing a confirmation button on a keypad. The confirmation may be provided to the server 110 and upon receiving the confirmation the server 110 may store an association between an identifier of the healthcare device 102 and an identifier of the patient in the data store 114. In this manner, the server 110 may identify any subsequent data items received from the healthcare device 102 as corresponding to the associated patient. Alternatively, or in addition, the server 110 may program the healthcare device 102 with parameters derived from any additional orders received from the POE system that are associated with the patient. The process of handling data corresponding to a patient associated with a healthcare device 102 is discussed further in FIG. 5 below.

Alternatively, or in addition, if the server 110 receives a communication from the healthcare device 102 indicating that the indicated patient is not the patient receiving healthcare from the healthcare device 102, the server 110 may store an indication that the patient is not associated with the healthcare device 102. The server 110 may then repeat steps 206-224 exclusive of any orders associated with the patient was identified as not receiving healthcare from the healthcare device 102.

At step 208, the server 110 may determine that the set of parameters correlates to more than one order when more than one order includes attributes that correlate directly to the set of parameters, or when none of the orders include attributes that correlate directly to the set of parameters. For example, the set of parameters may correlate to more than one order when multiple orders were received from the POE system that include attributes that directly correlate to the parameters.

Alternatively, or in addition, the set of parameters may correlate to more than one order when none of the orders directly correlate to the set of parameters. This scenario may occur, for example, if the healthcare professional programs the healthcare device 102 with incorrect parameters, e.g. parameters that do not correlate to the order from which the parameters were derived by the healthcare professional. In this instance, the server 110 may identify a number of the orders that partially correlate to the parameters, e.g. a number of the orders that most closely correlate to the parameters. For example, the server 110 may identify the orders that include the largest number of order attributes that correlate to parameters of the set of parameters. Alternatively, or in addition, the server 110 may apply different weights to different types of the parameters. For example, the server 110 may apply higher or lower weights to the type of medication, the amount of medication to be dispensed, the rate at which the medication is to be dispensed, or generally to any of the parameters.

If, at step 208, the server 110 determines that the received set of parameters correspond to more than one order, the server 110 may proceed to step 210. At step 210, the server 110 may identify one or more attributes associated with the healthcare device 102, such as an extrinsic attribute of the healthcare device 102, and/or an intrinsic attribute of the healthcare device 102, in order to attempt to disambiguate the multiple orders that correlate to the set of parameters.

For example, an intrinsic attribute of the healthcare device 102 may include the type of the healthcare device 102, such as the model and/or manufacturer of the healthcare device 102, a Media Access Control (MAC) address of the healthcare device 102, or generally any attribute of the healthcare device 102 that is intrinsic to the healthcare device 102. The server 110 may identify an intrinsic attribute from information received from the healthcare device 102, the server 110 may request an intrinsic attribute from the healthcare device 102, and/or the server 110 may retrieve an intrinsic attribute of the healthcare device 102 from another server 116, such as an asset management system. For example, the set of parameters received from the healthcare device 102 may include the MAC address of the healthcare device 102 and/or may include an identifier string that is indicative of the type of the healthcare device 102. Alternatively, or in addition, the server 110 may request either of these information items from the healthcare device 102. Alternatively, or in addition, the server 110 may retrieve these information items from another server 116, such as an asset management system that includes records describing each of the healthcare devices 102 in the hospital or caregiving institution.

In another example, an extrinsic attribute of the healthcare device 102 may include a location of the healthcare device 102, a network identifier of the healthcare device 102, an identifier of the healthcare professional that programmed the healthcare device 102, previous parameters programmed into the healthcare device 102, or generally any attribute associated with the healthcare device 102 that is extrinsic to the healthcare device 102. The server 110 may identify an extrinsic attribute from information received from the healthcare device 102, the server 110 may request an extrinsic attribute from the healthcare device 102, and/or the server 110 may retrieve an extrinsic attribute of the healthcare device 102 from another server 116, such as an asset management system. For example, the set of parameters received by the server 110 may include an identifier of the healthcare professional who programmed the healthcare device 102, and/or may include a network identifier of the healthcare device 102, such as an Internet Protocol (IP) address of the healthcare device 102. Alternatively, or in addition, the server 110 may instruct the healthcare device 102 to request that the healthcare professional inputs their identifier into the healthcare device 102, which may then be provided to the server 110.

Alternatively, or in addition, the server 110 may retrieve an extrinsic attribute from another server 116, such as an asset management system. For example, an asset management system may store extrinsic and intrinsic attributes for each of the healthcare devices 102 of the hospital or caregiving institution, such as the type of each of the healthcare devices 102, the location of each of the healthcare devices 102 in the hospital, the network identifier of each of the healthcare devices 102, the healthcare professional assigned to the location of a healthcare device 102, or generally any attributes corresponding to the healthcare devices 102. In this example, the server 110 may be able to use the network identifier of the healthcare device 102 to retrieve attributes of the healthcare device 102 from the asset management system.

Alternatively, or in addition, an employee management system may store information indicating a location or region of the hospital that each healthcare professional is assigned to. In this example, the server 110 may determine a region, or general location, of the healthcare device 102 based on the location or region of the hospital that is assigned to the healthcare professional who programmed the healthcare device 102. In this example, the server 110 may be able to utilize an identifier of the healthcare professional who programmed the healthcare device 102 to retrieve the region or location of the hospital assigned to the healthcare professional. The server 110 may then identify the region or location assigned to the healthcare professional as the region or location where the healthcare device 102 is located. Alternatively, or in addition, the server 110 may utilize a heuristic method based on one or more of the aforementioned techniques to identify one or more extrinsic and/or intrinsic attributes of the healthcare device 102.

At step 214, the server 110 may identify information determinable from the multiple orders that correlate to the set of parameters. For example, the server 110 may retrieve the locations of one or more of the patients associated with each of the orders, such as from a patient management system. Alternatively, or in addition, the server 110 may retrieve information from patient profiles, patient medical histories, patient billing records, or generally any data set that includes records associated with individual patients, e.g. patient identified information, such as previous orders generated for the patient, and any information determinable from the previous orders, such as the healthcare device 102 that provided the previous order, the healthcare professional that programmed the previous order into the healthcare device 102, etc. For example, the server 110 may identify one or more healthcare professionals that have previously provided healthcare to the patient, such as from the patient's medical records.

Alternatively, or in addition, the server 110 may determine a possible location of the healthcare device 102, such as from a hospital management system. For example, if the server 110 determines that the medication corresponding to an order is only dispensed in certain regions of the hospital, e.g. decontamination regions, etc., the server 110 may determine that the healthcare device 102 dispensing the order is located within one of the regions where the medication is dispensed. Similarly, if the server 110 can determine a region or general location corresponding to a healthcare device 102, the server 110 may retrieve an identifier of a healthcare professional assigned to the region, such as from an employee management system. The identifier of the healthcare professional may then be cross-referenced against the patient records to identify which of the patients have received healthcare from the healthcare professional. Alternatively, or in addition, the server 110 may utilize a heuristic method based on one or more of the aforementioned techniques to identify additional information determinable from an order.

At step 214, the server 110 may correlate the set of parameters to the multiple orders determined at step 206, where the correlation is further based on any extrinsic and/or intrinsic attributes determined for the healthcare device 102, and/or any additional information determinable from each of the orders. For example, if the server 110 determines that the patient associated with one of the correlated orders is located in the same region of the hospital as the location determined for the healthcare device 102, and if none of the remaining orders are associated with patients that are located in the same region of the hospital, the server 110 may determine that the set of parameters correspond to the order associated with the patient who is located in the same region of the hospital as the healthcare device 102. Alternatively, or in addition, the server 110 may use heuristics based on any of the extrinsic and/or intrinsic attributes identified for the healthcare device 102 and/or any additional information determined from the orders to correlate the parameters to a single order.

At step 216, the server 110 determines whether the parameters still correlate to more than one order based on the identified attributes of the healthcare device 102 and/or the additional information determined from the orders. If, at step 216, the server 110 determines that the parameters correlate to only one of the orders based on the identified attributes of the healthcare device 102 and/or the additional information determined from the orders, the server 110 may move to step 224. At step 224, the server 110 may associate the healthcare device 102 with the patient associated with the correlated order.

If, at step 216, the server 110 determines that the parameters still correlate to more than one of the remaining orders based on the identified attributes of the healthcare device 102 and/or the additional information determined from the orders, the server 110 may move to step 218. At step 218, the server 110 may provide an indication of the patients associated with the remaining correlated orders to the healthcare device 102. At step 220, the server 110 may receive a selection of one of the patients from the healthcare device 102. For example, the healthcare device 102 may present the indicated patients to the healthcare professional who programmed the healthcare device 102. The healthcare professional may then select the indicated patient that corresponds to the patient receiving healthcare from the healthcare device 102.

Alternatively, or in addition, if the server 110 is able to identify different levels of confidence corresponding to whether each of the indicated patients may be associated with the healthcare device 102, the server 110 may order the indications of the patients based on the confidence levels. For example, the server 110 may order the indication of the patient with the highest confidence level first, since this patient may be most likely to be the patient receiving healthcare from the healthcare device 102. As previously discussed, the server 110 may determine different levels of confidence for each of the patients based on how closely the orders that identify the patients correlate to the parameters.

Alternatively, or in addition, the server 110 may receive an indication from the healthcare device 102 that none of the indicated patients corresponds to the patient receiving healthcare from the healthcare device 102. In this instance, the server 110 may store an indication that none of the indicated patients are associated with the healthcare device 102, and the server 110 may then repeat steps 206-224 exclusive of any orders associated with the indicated patients.

At step 222, the server 110 may associate the health care device 102 with the selected patient. For example, the server 110 may store an association between an identifier of the healthcare device 102 and an identifier of the selected patient. In this manner, the server 110 may be able to associate any additional data received from the healthcare device 102 with the patient. Alternatively, or in addition, the server 110 may be able to remotely program the healthcare device 102 with any additional orders received from the POE system that identify the patient.

Figure 3:
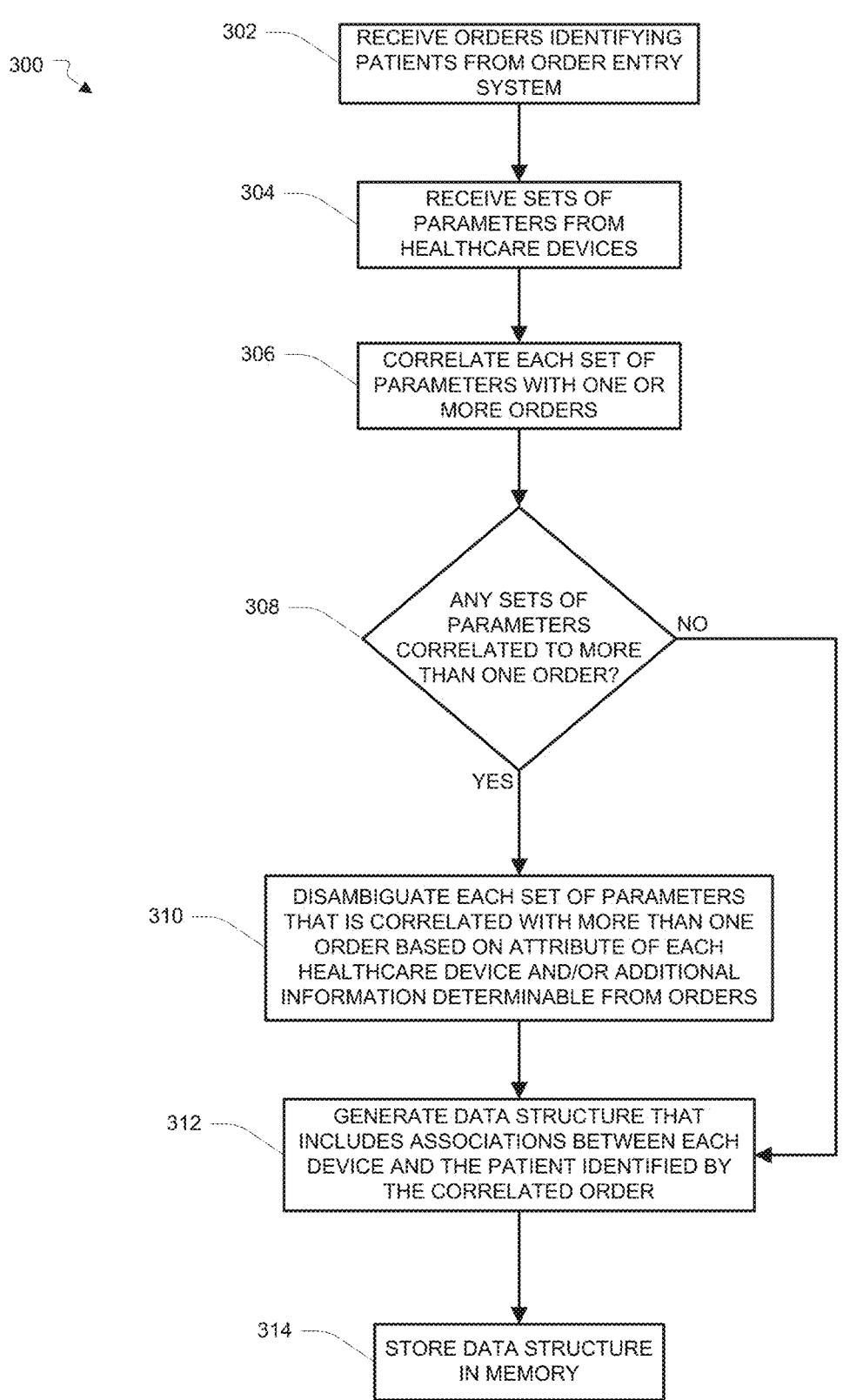
FIG. 3 illustrates a flow diagram of an example server process for associating patients with devices in a patient-device association system.

FIG. 3 illustrates a flow diagram of an example server process 300 for associating patients with devices in a patient-device association system. At step 302, the server 110 may receive orders that each identify a patient, such as from a POE system. The orders may each include one or more order attributes, such as attributes that characterize how the order is to be provided to the patient. At step 304, the server 110 may receive sets of parameters from healthcare devices 102, such as healthcare devices 102 located throughout the hospital or the caregiving institution. The parameters may be programmed into the healthcare devices 102 by healthcare professionals and based on attributes of orders generated by the POE system. At step 306, the server 110 may correlate each set of parameters with one or more of the orders received from the POE system. For example, the server 110 may correlate the sets of parameters with the orders based on the attributes of each of the orders.

At step 308, the server 110 determines whether any of the received sets of parameters correlate with more than one order. If, at step 308, the server 110 determines that at least one of the received sets of parameters correlates to more than one of the orders, the server 110 moves to step 310. At step 310, the server 110 disambiguates each set of parameters that is correlated with more than one order based on attributes of each healthcare device 102 from which each set of parameters was received and/or based on additional information that is determinable from each of the orders.

If the server 110 is unable to disambiguate the correlation of a set of parameters to a single order, the server 110 may provide an indication of all of the patients identified by all of the correlated orders to the healthcare device 102 from which the set of parameters was received. The healthcare professional that programmed the healthcare device 102 may select the indicated patient that corresponds to the patient that is receiving healthcare from the healthcare device 102. The selection may be provided to the server 110 such that the server 110 may associate the selected patient with the healthcare device 102.

At step 312, the server 110 generates a data structure that includes associations between each device and the patient identified by the correlated order, or the patient selected by the healthcare professional. The data structure may include mappings between the patients and the healthcare devices 102 in the hospital. In some instances, multiple devices may be mapped to a single patient. For example, a patient may be receiving medication from a medication dispensing device while the patient is being monitored by a patient monitoring device.

In this instance, the association between the patient and the device may further include an indication of the type of healthcare device 102, e.g. a monitoring device, a dispensing device, etc. In this manner, if the server 110 receives an additional order that identifies the patient, the server 110 may be able to quickly identify which of the multiple healthcare devices 102 associated with the patient is capable of dispensing medication to the patient.

Alternatively, or in addition, multiple patients may be mapped to a single healthcare device 102. In this instance, the data received from a healthcare device 102 that is associated with multiple patients may include an identifier from which the patient corresponding to the data can be determined.

At step 314, the server 110 stores the data structure in memory, such as the data store 114. The server 110 may subsequently access the data structure to determine the patient mapped to a particular healthcare device 102, such as when the server 110 receives data from the healthcare device 102. Alternatively, or in addition, the server 110 may subsequently access the data structure to determine the healthcare device 102 associated with a patient, such as when the server 110 receives an additional order for the patient from the POE system.

Alternatively, or in addition, the server 110 may generate one or more reports that aggregate the patient identified data. The reports may be provided to healthcare professionals, such as to assist the healthcare professionals with providing healthcare to the patients and/or to assist the healthcare professionals with diagnosing the patients. For example, a report for a patient may provide information corresponding to any medications that were dispensed by medication dispensing devices to the patient along with information corresponding to vital signs measurements taken by patient monitoring devices for the patient. The patient monitoring information may overlay the medication dispensing information, such as along a time axis. In this manner, a healthcare professional may identify whether changes in the dispensing of the medication had any impact on the patient's vital signs.

FIG. 4 illustrates a flow diagram of an alternative example server process 400 for associating a patient with a device in a patient-device association system. At step 402, the server 110 may receive data items that are associated with, or that identify, patients. For example, the server 110 may receive orders from a POE system where each order identifies a particular patient. Alternatively, or in addition, the server 110 may receive a profile identifying a patient from a patient management system. Generally, the server 110 may receive any data items that identify, or are associated with, a patient. In one example, the data items may be received, or retrieved, from multiple independent sources.

At step 404, the server 110 may receive a set of parameters from a healthcare device 102 that are exclusive of a patient identifier or other patient identifying information, such as patient de-identified data. At step 406, the server 110 may correlate the set of parameters, e.g. the patient de-identified data, with at least one of the data items, e.g. the patient identified data. The server 110 may correlate the set of parameters with one of the data items using one or more of the techniques described herein, or a heuristic method based on a combination of one or more of the techniques described herein.

At step 410, the server 110 may store an association between the patient identified by the data item and the healthcare device 102 from which the set of parameters was received. For example, the server 110 may store the association in memory, such as the data store 114. In this manner, the server 110 is able to utilize patient-identified data items to determine a patient that is associated with patient de-identified data, such as the set of parameters received from the healthcare device 102.

FIG. 5 illustrates a flow diagram of an example server process for handling data corresponding to a patient associated with a healthcare device 102 in a patient-device association system. At step 502, the server 110 may receive data items from a healthcare device 102, such a patient de-identified data items. At step 504, the server 110 may retrieve the identifier of the patient associated with the healthcare device 102 based on an identifier of the healthcare device 102, such as from a patient-device mapping data structure stored in the data store 114. At step 506, the server 110 may associate the data items received from the healthcare device 102 with the retrieved patient identifier, such as by storing the received data items with the patient identifier.

At step 508, the server 110 may receive an additional order from an order entry system. The additional order may identify a patient for the order, but may not identify the healthcare device 102 that will provide the order. At step 510, the server 110 may determine the healthcare device 102 associated with the patient, such as from a patient-device mapping data structure stored in the data store 114. At step 512, the server 110 may generate parameters for programming the healthcare device 102 based on the additional order. For example, the additional order may indicate various attributes related to providing the order to the patient, such as the amount of medication to be provided, the rate at which the medication is to be provided, the time period when the medication is to be provided, etc. The server 110 may generate the parameters based on the attributes of the order.

At step 514, the server 110 may remotely program the healthcare device 102 using the generated parameters. For example, the server 110 may transmit instructions over the network 108 to the healthcare device 102, or to an adapter 104 communicably coupled to the healthcare device 102, that cause the healthcare device 102 to be programmed with the generated parameters. Alternatively, or in addition, the server 110 may transmit a request to program parameters into the healthcare device 102 to the healthcare device 102, or to an adapter 104 communicably coupled to the healthcare device 102. Alternatively, or in addition, the server 110 may program the healthcare device 102 by using an remote application programming interface (API) call associated with the healthcare device 102, such as over the network 108.

Alternatively, or in addition, the server 110 may verify whether the additional order includes attributes that can be programmed into the healthcare device 102. For example, the server 110 may retrieve a list of possible programming parameters for the healthcare device 102, such as from an asset management system. If the server 110 determines that parameters for the healthcare device 102 can not be generated based on the additional order, the server 110 may transmit an alert to a healthcare professional assigned to the location of the patient. For example, the server 110 may transmit an instant message, a text message, an email, an automated phone message, or generally any method of communicating a message to a healthcare professional. The message may include the attributes of the additional order such that the healthcare professional can identify an appropriate healthcare device 102 for providing the additional order to the patient.

FIG. 6 illustrates a flow diagram of an example device process 600 for confirming a patient-device association in a patient-device association system. At step 602, a healthcare device 102 that provides healthcare to a patient may receive a set of parameters. For example, a healthcare professional may program the healthcare device 102 with parameters that correspond to an order generated for the patient. At step 604, the healthcare device 102 may provide the parameters to a remote device, such as the server 110, over the network 108.

At step 606, the healthcare device 102 may receive one or more patient identifiers from the remote device, such as the server 110. At step 608, the healthcare device 102 may present the one or more patient identifiers, such as to the healthcare professional that programmed the healthcare device 102. At step 608, the healthcare device 102 may receive a selection of one of the patient identifiers, such as from the healthcare professional that programmed the healthcare device 102. At step 612, the healthcare device 102 may provide the selected patient identifier to the remote device, such as the server 110, over the network 108.

Figure 7:
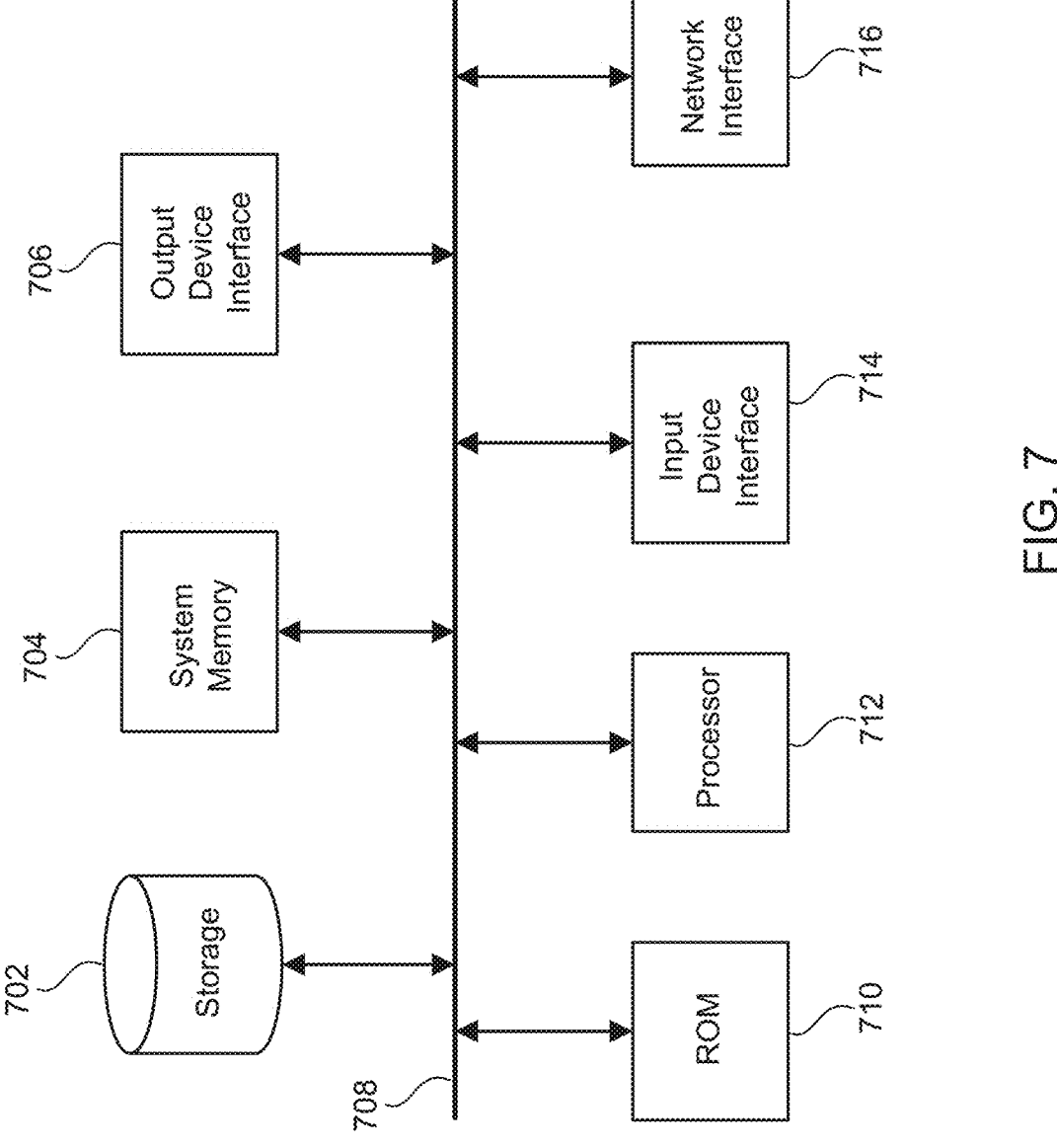
FIG. 7 conceptually illustrates an electronic system with which some implementations of the subject technology may be implemented.

FIG. 7 conceptually illustrates an electronic system with which some implementations of the subject technology are implemented. Electronic system 700 can be a server, computer, phone, PDA, a tablet computer, a television with one or more processors embedded therein or coupled thereto, or generally any electronic device. Such an electronic system includes various types of computer readable media and interfaces for various other types of computer readable media. Electronic system 700 includes a bus 708, processing unit(s) 712, a system memory 704, a read-only memory (ROM) 710, a permanent storage device 702, an input device interface 714, an output device interface 706, and a network interface 716.

Bus 708 collectively represents all system, peripheral, and chipset buses that communicatively connect the numerous internal devices of electronic system 700. For instance, bus 708 communicatively connects processing unit(s) 712 with ROM 710, system memory 704, and permanent storage device 702.

From these various memory units, processing unit(s) 712 retrieves instructions to execute and data to process in order to execute the processes of the subject disclosure. The processing unit(s) can be a single processor or a multi-core processor in different implementations.

ROM 710 stores static data and instructions that are needed by processing unit(s) 712 and other modules of the electronic system. Permanent storage device 702, on the other hand, is a read-and-write memory device. This device is a non-volatile memory unit that stores instructions and data even when electronic system 700 is off. Some implementations of the subject disclosure use a mass-storage device (such as a magnetic or optical disk and its corresponding disk drive) as permanent storage device 702.

Other implementations use a removable storage device (such as a floppy disk, flash drive, and its corresponding disk drive) as permanent storage device 702. Like permanent storage device 702, system memory 704 is a read-and-write memory device. However, unlike storage device 702, system memory 704 is a volatile read-and-write memory, such a random access memory. System memory 704 stores some of the instructions and data that the processor needs at runtime. In some implementations, the processes of the subject disclosure are stored in system memory 704, permanent storage device 702, and/or ROM 710. For example, the various memory units may include instructions for processing, generating, and/or providing verification requests and/or verification responses in accordance with some implementations. From these various memory units, processing unit(s) 712 retrieves instructions to execute and data to process in order to execute the processes of some implementations.

Bus 708 also connects to input and output device interfaces 714 and 706. Input device interface 714 enables the user to communicate information and select commands to the electronic system. Input devices used with input device interface 714 include, for example, alphanumeric keyboards and pointing devices (also called "cursor control devices"). Output device interfaces 706 enables, for example, the display of images generated by the electronic system 700. Output devices used with output device interface 706 include, for example, printers and display devices, such as cathode ray tubes (CRT) or liquid crystal displays (LCD). Some implementations include devices such as a touchscreen that functions as both input and output devices.

Finally, as shown in FIG. 7, bus 708 also couples electronic system 700 to a network (not shown) through a network interface 716. In this manner, the computer can be a part of a network of computers (such as a local area network ("LAN"), a wide area network ("WAN"), or an Intranet, or a network of networks, such as the Internet. Any or all components of electronic system 700 can be used in conjunction with the subject disclosure.

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

A computer system further includes a data storage device such as a magnetic disk or optical disk, coupled to a bus for storing information and instructions. Computer systems may be coupled via input/output modules to various devices. The input/output module can be any input/output module, such as USB ports. The input/output module is configured to connect to a communications module, such as networking interface cards, as Ethernet cards, and modems. In certain aspects, the computer system includes an input/output module such as a keyboard and a pointing device, e.g., a mouse or a trackball, by which a user can provide input to the computer system. Other kinds of input devices can be used to provide for interaction with a user as well, such as a tactile input device, visual input device, audio input device, or brain-computer interface device. For example, feedback provided to the user can be any form of sensory feedback, e.g., visual feedback, auditory feedback, or tactile feedback; and input from the user can be received in any form, including acoustic, speech, tactile, or brain wave input. Exemplary output devices include display devices, such as a CRT (cathode ray tube) or LCD (liquid crystal display) monitor, for displaying information to the user.

According to one aspect of the present disclosure, the disclosed processes can be implemented using a processor executing one or more sequences of one or more instructions contained in memory. Such instructions may be read into memory from another machine-readable medium, such as a magnetic disk or an optical disk. Execution of the sequences of instructions contained in main memory causes processor to perform the process steps described herein. One or more processors in a multi-processing arrangement may also be employed to execute the sequences of instructions contained in memory. In alternative aspects, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. The communication can include, for example, any one or more of a personal area network (PAN), a local area network (LAN), a campus area network (CAN), a metropolitan area network (MAN), a wide area network (WAN), a broadband network (BBN), the Internet, and the like. Further, the communication network can include, but is not limited to, for example, any one or more of the following network topologies, including a bus network, a star network, a ring network, a mesh network, a star-bus network, tree or hierarchical network, or the like. The communications modules can be, for example, modems or Ethernet cards.

A computing system can include clients and servers. A client and server are generally remote from each other and typically interact through a communication network. The relationship of client and server arises by virtue of computer programs running on the respective computers and having a client-server relationship to each other. Computing systems can be, for example, and without limitation, a desktop computer, laptop computer, or tablet computer. Computing systems can also be embedded in another device, for example, and without limitation, a mobile telephone, a personal digital assistant (PDA), a mobile audio player, a Global Positioning System (GPS) receiver, a video game console, and/or a television set top box.

The term "machine-readable storage medium" or "computer readable medium" as used herein refers to any medium or media that participates in providing instructions to a processor for execution. Such a medium may take many forms, including, but not limited to, non-volatile media, volatile media, and transmission media. Non-volatile media include, for example, optical or magnetic disks. Volatile media include dynamic memory. Transmission media include coaxial cables, copper wire, and fiber optics. Common forms of machine-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

While operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The subject matter of this specification has been described in terms of particular aspects, but other aspects can be implemented and are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

The previous description is provided to enable any person skilled in the art to practice the various aspects described herein. While the foregoing has described what are considered to be the best mode and/or other examples, it is understood that various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the terms "a set" and "some" refer to one or more. Pronouns in the masculine (e.g., his) include the feminine and neuter gender (e.g., her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. A phrase such an embodiment may refer to one or more embodiments and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A system, comprising:

a data store, wherein the data store is accessible via a network;

one or more processors; and a non-transitory memory comprising instructions thereon that, when executed by the one or more processors, causes the one or more processors to perform operations for associating a medication dispensing device with a respective patient, comprising:

receiving a set of parameters to program the medication dispensing device to dispense medication to a patient unknown to the medication dispensing device, the set of parameters not including data identifying the unknown patient;

responsive to receiving the set of parameters:

providing the set of parameters to a remote computing system in order to obtain one or more patient identifiers for identifying the unknown patient; and receiving, from the remote computing system, one or more respective patient identifiers responsive to the set of parameters being provided to the remote computing system;

providing the one or more respective patient identifiers received from the remote computing system for display at a display screen associated with the medication dispensing device;

receiving, after the display of the one or more respective patient identifiers at the display screen, a user selection of a selected patient identifier, of the one or more patient identifiers, that identifies the patient; and causing an association between the selected patient identifier and the medication dispensing device to be recorded in the data store;

providing the selected patient identifier to the remote computing system;

receiving an order associated with the selected patient identifier from the remote computing system; and after receiving the order, automatically configuring the medication dispensing device to initiate dispense of a medication according to the set of parameters and the order received from the remote computing system.

2. The system of claim 1, the operations further comprising, based on providing the selected identifier to the remote computing system:

obtaining one or more device operating parameters based on the selected patient identifier for programming the medication dispensing device; and causing the programming of the medication dispensing device according to the set of parameters and the one or more device operating parameters, wherein the one or more device operating parameters are identified by the remote computing system from the order associated with the selected patient identifier.

3. The system of claim 2, wherein the one or more respective patient identifiers are identified from one or more healthcare orders by a search of the one or more healthcare orders based on the set of parameters.

4. The system of claim 3, the operations further comprising:

obtaining an extrinsic attribute of the medication dispensing device, the extrinsic attribute comprising a location of the medication dispensing device, a network identifier of the medication dispensing device, or a user identifier of a healthcare professional associated with the medication dispensing device, wherein the one or more respective patient identifiers are identified based on the extrinsic attribute in combination with the set of parameters.

5. The system of claim 4, the operations further comprising:

determining a location associated with the healthcare professional or the medication dispensing device; and identifying the one or more respective patient identifiers based on a determination that each patient associated with the one or more respective patient identifiers is associated with the location.

6. The system of claim 1, wherein causing the association comprises providing the selected patient identifier and an identity of the medication dispensing device to the remote computing system.

7. The system of claim 1, the operations further comprising:

receiving, from the remote computing system, a set of additional parameters that relate to providing additional healthcare to the patient; and causing, based on receiving the set of additional parameters, the medication dispensing device to provide additional healthcare to the patient in accordance with the set of additional parameters.

8. The system of claim 1, wherein at least one parameter of the set of parameters comprises an amount of an item to be dispensed, a time when an item is to be dispensed, or a rate at which the item is to be dispensed.

9. The system of claim 8, wherein the item comprises a substance prescribed for a medical treatment.

10. The system of claim 1, wherein the set of parameters comprise instructions for providing healthcare to the patient.

11. A method for associating a medication dispensing device with a respective patient, the method comprising:

receiving a set of parameters to program the medication dispensing device to dispense medication to a patient unknown to the medication dispensing device, the set of parameters not including data identifying the patient;

responsive to receiving the set of parameters:

providing the set of parameters to a remote computing system in order to obtain one or more patient identifiers for identifying the unknown patient; and receiving, from the remote computing system, one or more respective patient identifiers responsive to the set of parameters being provided to the remote computing system;

providing the one or more respective patient identifiers received from the remote computing system for display at a display screen associated with the medication dispensing device;

receiving, after the display of the one or more respective patient identifiers at the display screen, a user selection of a selected patient identifier, of the one or more patient identifiers, that identifies the patient; and causing an association between the selected patient identifier and the medication dispensing device to be recorded in a network accessible data store;

providing the selected patient identifier to the remote computing system;

receiving an order associated with the selected patient identifier from the remote computing system; and after receiving the order, automatically configuring the medication dispensing device to initiate dispense of a medication according to the set of parameters and the order received from the remote computing system.

12. The method of claim 11, further comprising, based on providing the selected identifier to the remote computing system:

obtaining one or more device operating parameters based on the selected patient identifier for programming the medication dispensing device; and causing the programming of the medication dispensing device according to the set of parameters and the one or more device operating parameters, wherein the one or more device operating parameters are identified by the remote computing system from the order associated with the selected patient identifier.

13. The method of claim 12, wherein the one or more respective patient identifiers are identified from one or more healthcare orders by a search of the one or more healthcare orders based on the set of parameters.

14. The method of claim 13, further comprising:

obtaining an extrinsic attribute of the medication dispensing device, the extrinsic attribute comprising a location of the medication dispensing device, a network identifier of the medication dispensing device, or a user identifier of a healthcare professional associated with the medication dispensing device, wherein the one or more respective patient identifiers are identified based on the extrinsic attribute in combination with the set of parameters.

15. The method of claim 14, further comprising:

determining a location associated with the healthcare professional or the medication dispensing device; and identifying the one or more respective patient identifiers based on a determination that each patient associated with the one or more respective patient identifiers is associated with the location.

16. The method of claim 11, wherein causing the association comprises providing the selected patient identifier and an identity of the medication dispensing device to the remote computing system.

17. The method of claim 11, further comprising:

receiving, from the remote computing system, a set of additional parameters that relate to providing additional healthcare to the patient; and causing, based on receiving the set of additional parameters, the medication dispensing device to provide additional healthcare to the patient in accordance with the set of additional parameters.

18. The method of claim 11, wherein at least one parameter of the set of parameters comprises an amount of an item to be dispensed, a time when an item is to be dispensed, or a rate at which the item is to be dispensed.

19. The method of claim 11, wherein the set of parameters comprise instructions for providing healthcare to the patient.

20. A non-transitory machine-readable medium comprising instructions stored thereon that, when executed by one or more processors, cause the one or more processors to perform operations for associating a medication dispensing device with a respective patient, comprising:

receiving a set of parameters to program a medication dispensing device to dispense medication to a patient unknown to the medication dispensing device, the set of parameters not including data identifying the patient;

responsive to receiving the set of parameters:

providing the set of parameters to a remote computing system in order to obtain one or more patient identifiers for identifying the unknown patient; and receiving, from the remote computing system, one or more respective patient identifiers responsive to the set of parameters being provided to the remote computing system;

providing the one or more respective patient identifiers received from the remote computing system for display at a display screen associated with the medication dispensing device;

receiving, based on the display at the display screen of the one or more respective patient identifiers, a user selection of a selected patient identifier, of the one or more patient identifiers, that identifies the patient; and causing an association between the selected patient identifier and the medication dispensing device to be recorded in a network accessible data store;

providing the selected patient identifier to the remote computing system;

receiving an order associated with the selected patient identifier from the remote computing system; and after receiving the order, automatically configuring the medication dispensing device to initiate dispense of a medication according to the set of parameters and the order received from the remote computing system.

\* \* \* \* \*